(12) United States Patent
Tadros et al.

(10) Patent No.: US 7,210,926 B2
(45) Date of Patent: May 1, 2007

(54) FORMABLE SHEETS FOR MEDICAL APPLICATIONS AND METHODS OF MANUFACTURE THEREOF

(75) Inventors: Safwat Tadros, Evansville, IN (US); Shreyas Chakravarti, Evansville, IN (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/705,590

(22) Filed: Nov. 10, 2003

(65) Prior Publication Data

US 2005/0100853 A1 May 12, 2005

(51) Int. Cl.
*A61C 3/00* (2006.01)
(52) U.S. Cl. .......................................... 433/6; 128/859
(58) Field of Classification Search ................... 433/6, 433/5, 24, 18, 7, 37; 128/859, 861, 862
See application file for complete search history.

(56) References Cited

U.S. PATENT DOCUMENTS

| | | | |
|---|---|---|---|
| 4,894,012 A * | 1/1990 | Goldberg et al. ........... 433/215 |
| 5,975,893 A | 11/1999 | Chishti et al. ................. 433/6 |
| 6,183,248 B1 * | 2/2001 | Chishti et al. ................. 433/6 |
| 6,386,864 B1 | 5/2002 | Kuo ............................... 433/6 |
| 6,497,574 B1 | 12/2002 | Miller ......................... 433/213 |
| 6,524,101 B1 | 2/2003 | Phan et al. ..................... 433/6 |
| 2002/0082360 A1 * | 6/2002 | Conn et al. ................. 525/439 |
| 2002/0187451 A1 | 12/2002 | Phan et al. ..................... 433/6 |
| 2003/0003416 A1 | 1/2003 | Chishti et al. ............... 433/24 |
| 2003/0039941 A1 | 2/2003 | Chishti et al. ............... 433/24 |
| 2003/0049584 A1 | 3/2003 | Chishti et al. ............... 433/24 |
| 2003/0198912 A1 * | 10/2003 | Mah .............................. 433/6 |

OTHER PUBLICATIONS

ASTM Designation: D 1003-00 Standard Test Method for Haze and Luminous Transmittance of Transparent Plastics, Jun. 10, 2000, pp. 1-6.

* cited by examiner

Primary Examiner—Melba Bumgarner
(74) Attorney, Agent, or Firm—Cantor Colburn LLP

(57) ABSTRACT

Disclosed herein is an appliance for use in an oral cavity, wherein the appliance comprises a polymeric shell that comprises a polymeric mixture, and further wherein the polymeric shell has cavities designed to receive teeth. Disclosed herein too is a method for maintaining or repositioning teeth in the oral cavity comprising placing an appliance in a patient's mouth, wherein the appliance comprises a polymeric shell that comprises a polymeric mixture, and further wherein the polymeric shell has cavities designed to receive teeth.

18 Claims, 4 Drawing Sheets

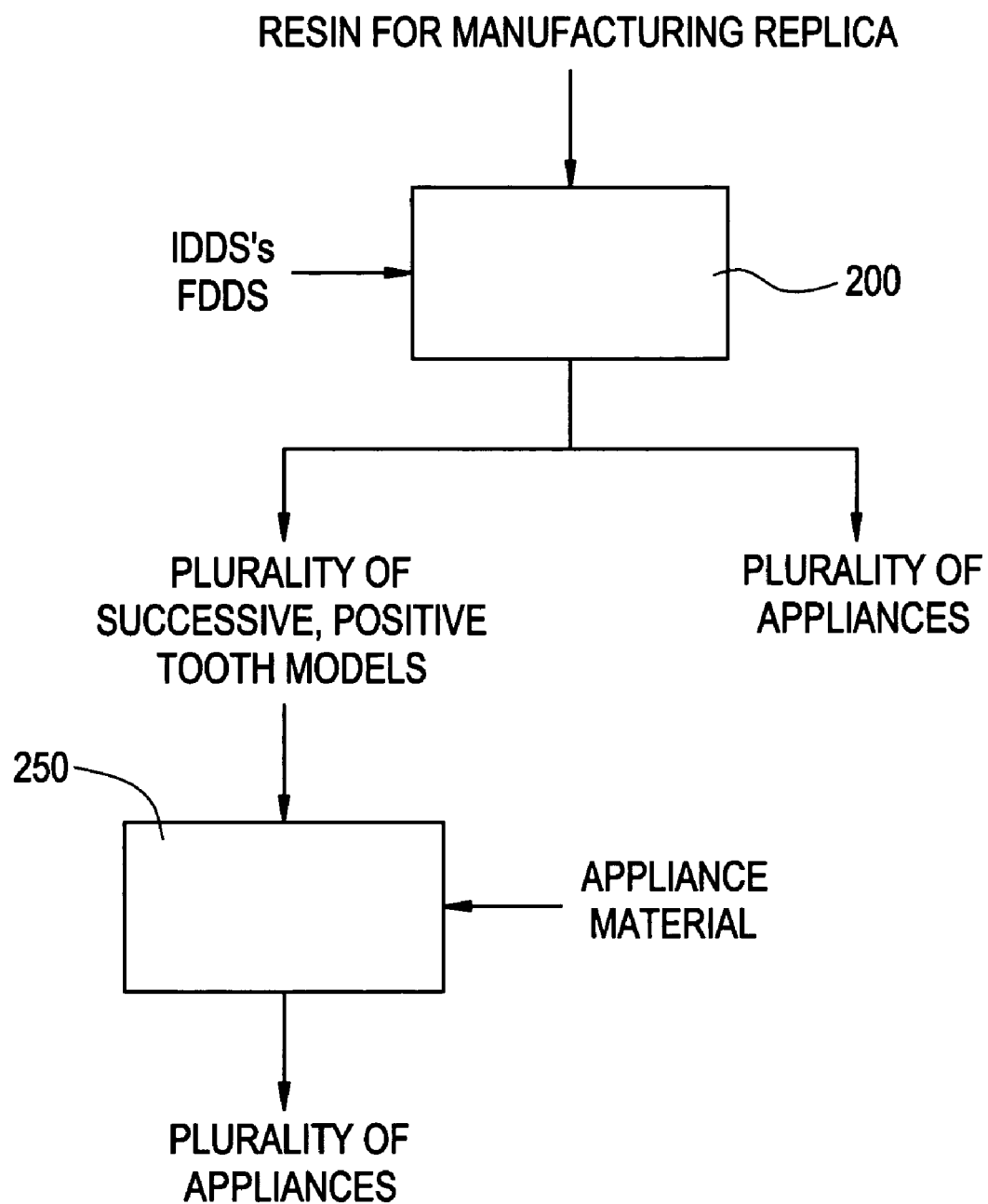

FORMABLE SHEETS FOR MEDICAL APPLICATIONS AND METHODS OF MANUFACTURE THEREOF

BACKGROUND

This disclosure relates to formable sheets for medical applications and methods of manufacture thereof.

Repositioning teeth for aesthetic or other reasons is generally accomplished by wearing devices called "braces". Braces comprise a variety of components such as brackets, archwires, ligatures, and O-rings. Attaching these components to a patient's teeth is a tedious and time-consuming procedure requiring many meetings with the treating orthodontist. This reduces the orthodontist's patient capacity and thus makes orthodontic treatment quite expensive.

The primary force-inducing component in a set of braces is the archwire. The archwire is resilient and is attached to the brackets by way of slots in the brackets. The archwire links the brackets together and exerts forces on them to move the teeth over time. Twisted wires or elastomeric O-rings are generally used to reinforce attachment of the archwire to the brackets. Attachment of the archwire to the brackets is called "ligation" and wires used in this procedure are called "ligatures." The elastomeric O-rings are called "plastics."

After the archwire is in place, periodic meetings with the orthodontist are required, during which the patient's braces will be adjusted by installing a different archwire having different force-inducing properties or by replacing or tightening existing ligatures. These meetings are generally scheduled every three to six weeks.

As detailed above, the application of braces to patient's teeth is a tedious and time consuming process and requires many visits to the orthodontist's office. Further, the use of braces is unsightly, aesthetically unpleasing, uncomfortable, presents a risk of infection, and makes brushing, flossing, and other dental hygiene procedures difficult. For these reasons, it is desirable to provide alternative methods and systems for repositioning the teeth.

SUMMARY

Disclosed herein is an appliance for use in an oral cavity, wherein the appliance comprises a polymeric shell that comprises a polymeric mixture, and further wherein the polymeric shell has cavities designed to receive teeth.

Disclosed herein too is a method for maintaining or repositioning teeth in the oral cavity comprising placing an appliance in a patient's mouth, wherein the appliance comprises a polymeric shell that comprises a polymeric mixture, and further wherein the polymeric shell has cavities designed to receive teeth.

Disclosed herein too is a method for maintaining or repositioning teeth in the oral cavity comprising placing an appliance in a patient's mouth, wherein the appliance comprises a polymeric shell that comprises a polymeric mixture, and further wherein the polymeric shell has cavities designed to receive teeth.

The above-described and other features will be appreciated and understood by those skilled in the art from the following detailed description, drawings, and appended claims.

DESCRIPTION OF FIGURES

FIG. 5 illustrates alternative processes for producing a plurality of appliances utilizing digital data sets representing the intermediate and final appliance designs.

DETAILED DESCRIPTION OF PREFERRED EMBODIMENTS

Disclosed herein is an appliance made from a sheet comprising a polymeric mixture that may be advantageously used for repositioning teeth from an initial tooth arrangement to a final tooth arrangement. In one embodiment, the appliance displays properties of optical clarity, stain resistance, and transparency, which makes the appliance invisible when used in the oral cavity. The appliance is also easy to install and is more comfortable to wear than braces. The polymeric mixture used in the appliance displays properties of toughness and creep resistance, which facilitates the incremental repositioning of individual teeth in a series of less than or equal to about 40 steps, preferably less than or equal to about 25 steps, more preferably less than or equal to about 10 steps, and even more preferably less than or equal to about 5 steps.

The polymeric mixtures may also be advantageously used in other medical devices as well as in other dental applications such as dental retainer appliances that may be used for retaining teeth in a desired position and other devices that can be used to prevent patients from grinding their teeth during their sleep. In one embodiment, the polymer mixture may be used to manufacture an appliance for use in an oral cavity, wherein the appliance comprises a polymeric shell that has cavities designed to receive teeth. In another embodiment, the appliance is part of a system of appliances designed to reposition teeth in a series of steps. In yet another embodiment, the polymeric shell comprises two or more layers, wherein on layer comprises an elastomer.

A "step" refers to one use of the appliance for a prescribed period of time on either the upper or lower teeth to facilitate either the repositioning of the teeth or the retaining of the teeth in a particular position. The term "teeth" as defined herein may apply to a single tooth or to a plurality of teeth.

The successive use of a number of such appliances permits each appliance to be configured to move individual teeth in small increments. A desirable increment for movement of the teeth is less than or equal to about 2 mm, preferably less than or equal to about 1 mm, and more preferably less than or equal to about 0.5 mm. These increments refer to the maximum linear translation of any point on a tooth as a result of using a single appliance. The movements provided by successive appliances, may not be the same for any particular tooth. Thus, one point on a tooth may be moved by a particular distance as a result of the use of one appliance and thereafter moved by a different distance and/or in a different direction by the use of a later appliance.

Figure 1:
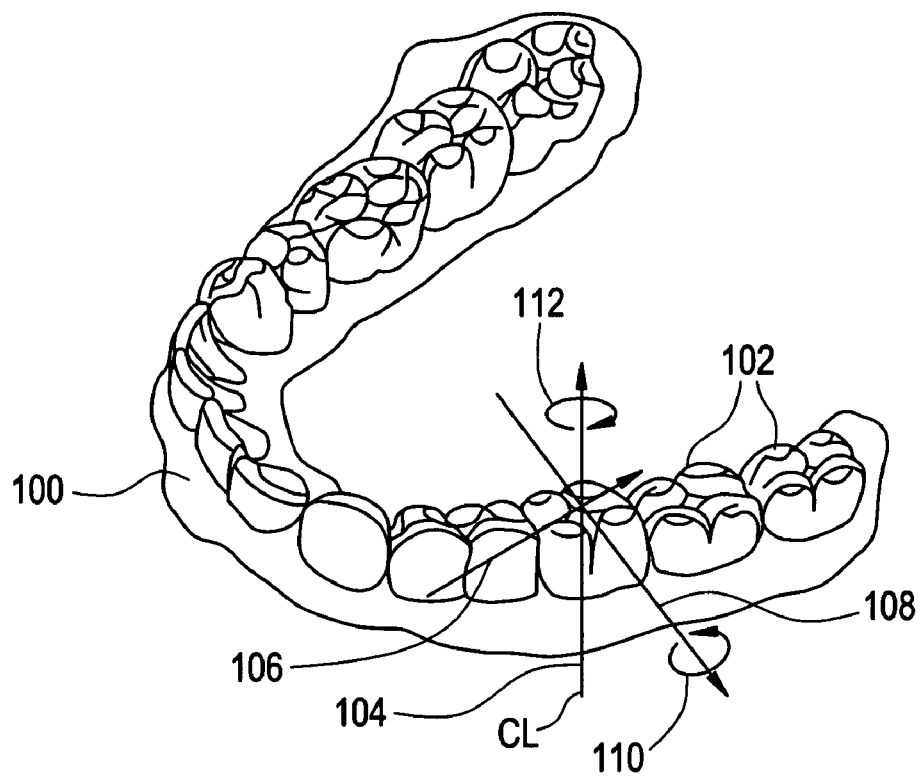
FIG. 1 illustrates a patient's jaw and provides a general indication of how teeth may be moved by the appliance.

Referring now to FIG. 1, a representative jaw 100 generally contains up to sixteen teeth 102. The appliance may be used to move at least some of these teeth from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 114. Thus, all possible free-form motions of the tooth can be performed.

Figure 2:
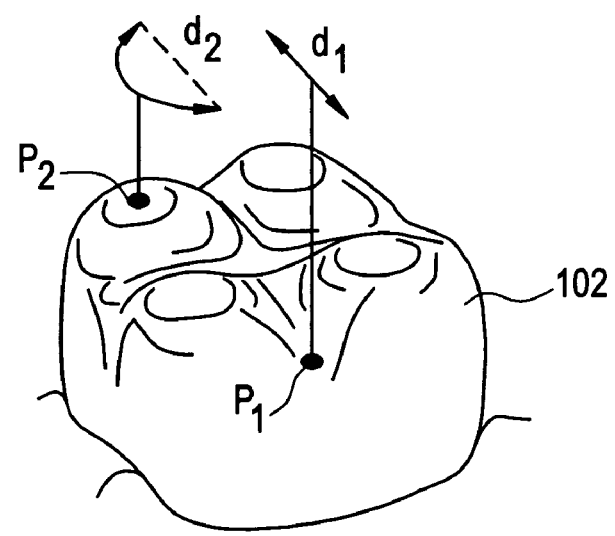
FIG. 2 illustrates a single tooth from FIG. 1 and defines how tooth movement distances are engineered.

Referring now to FIG. 2, the magnitude of any tooth movement achieved by the methods and systems will be defined in terms of the maximum linear translation of any point P on a tooth 102. Each point $P_i$ will undergo a cumulative translation as that tooth is moved in any of the orthogonal or rotational directions defined in FIG. 1. Thus, an arbitrary point $P_1$ may in fact undergo a true side-to-side translation as indicated by arrow $d_1$, while a second arbitrary point $P_2$ may travel along an arcuate path, resulting in a final translation $d_2$.

Figure 3:
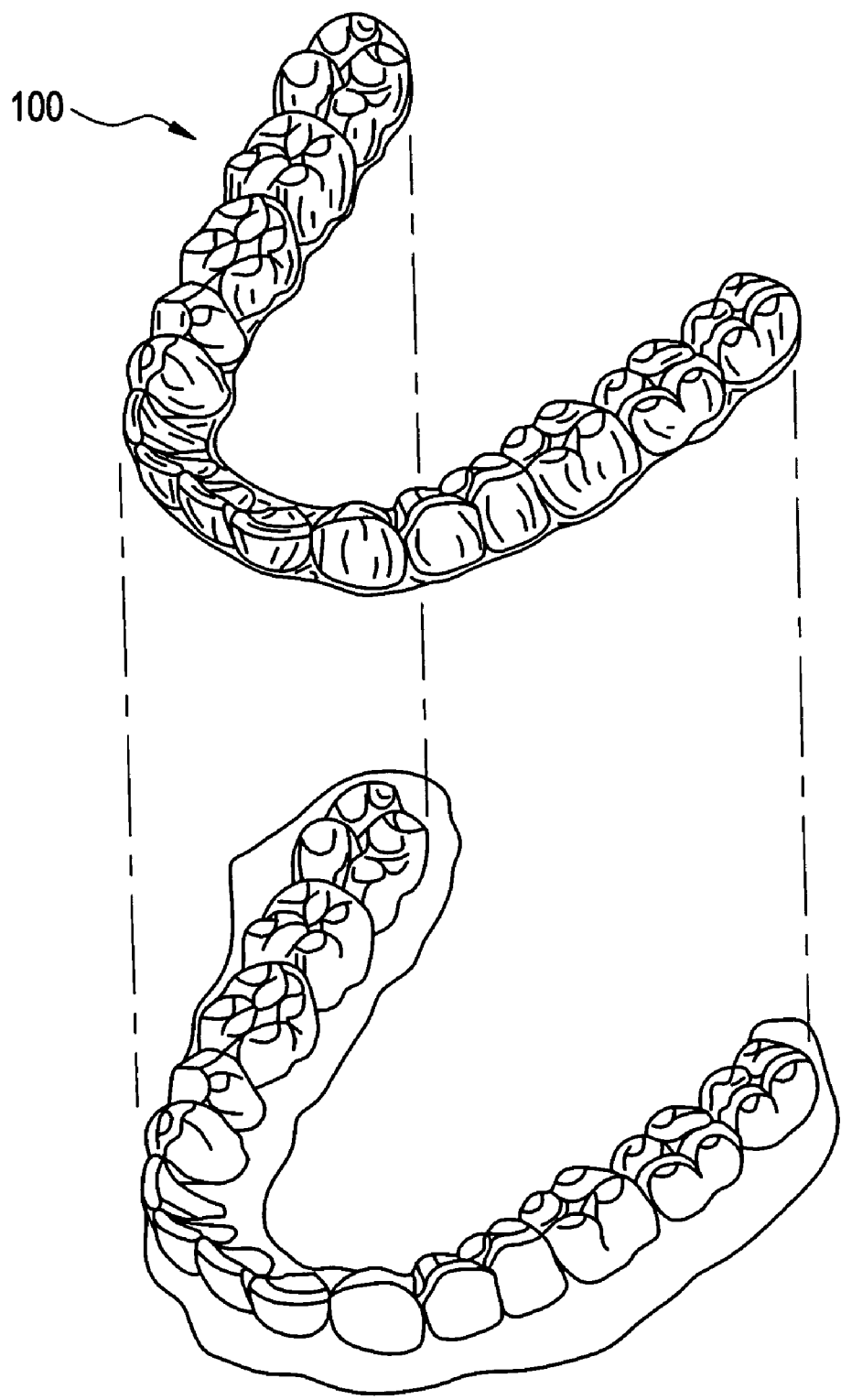
FIG. 3 illustrates the jaw of FIG. 1 together with an incremental position adjustment appliance.
Figure 4:
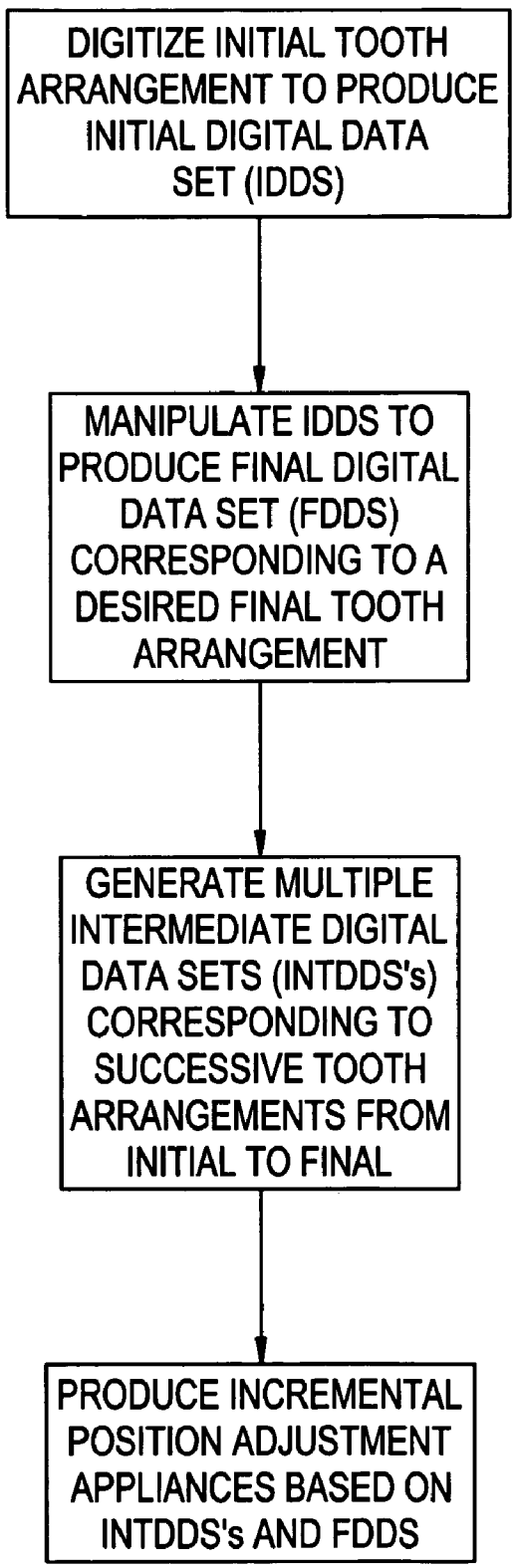
FIG. 4 is a block diagram illustrating the steps for producing a system of incremental position adjustment appliances.

Referring now to FIG. 3, a system for effecting incremental repositioning of individual teeth comprises a plurality of incremental position adjustment appliances. The appliances are intended to effect incremental repositioning of individual teeth in the jaw and are intended to be worn by a patient successively in order to achieve the gradual tooth repositioning as described herein. A preferred appliance 100 will comprise a polymeric shell having a cavity shaped to receive and resiliently reposition teeth from one tooth arrangement to a successive tooth arrangement. The polymeric shell will preferably fit over all teeth present in the upper or lower jaw. Often, only a certain tooth or teeth will be repositioned while other teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth that are moved can also serve as a base or anchor region for holding the repositioning appliance. Additionally, the gums and/or the palette can serve as an anchor region, thus allowing all or nearly all of the teeth to be repositioned simultaneously.

The appliance 100 of FIG. 3 preferably contains at least one layer manufactured from a sheet of a polymeric mixture. Polymeric mixtures used for such appliances, are generally physical mixtures of two or more thermoplastic polymers. Thermoplastic polymers that may be used in the polymeric mixture may be oligomers, polymers, ionomers, dendrimers, copolymers such as block copolymers, graft copolymers, star block copolymers, random copolymers, and the like, as well as combinations comprising at least one of the foregoing polymers. Suitable examples of thermoplastic polymers are polyolefins such as polyethylene, polypropylene; polyamides such as Nylon 4,6, Nylon 6, Nylon 6,6, Nylon 6, 10, Nylon 6, 12; polyesters such as polyethelene terephthalate (PET), polybutylene terephthalate (PBT), poly(1,4-cyclohexane-dimethanol-1,4-cyclohexanedicarboxylate) (PCCD), poly(trimethylene terephthalate) (PTT), poly(cyclohexanedimethanol-co-ethylene terephthalate) (PETG), poly(ethylene naphthalate) (PEN), poly(butylene naphthalate) (PBN); polyarylates, polyimides, polyacetals, polyacrylics, polycarbonates (PC), polystyrenes, polyamideimides, polyacrylates, polymethacrylates such as polymethylacrylate, or polymethylmethacrylate (PMMA); polyurethanes, polyarylsulfones, polyethersulfones, polyarylene sulfides, polyvinyl chlorides, polysulfones, polyetherimides, polytetrafluoroethylenes, polyetherketones, polyether etherketones, polyarylene ethers, polydimethylsiloxane, liquid crystalline polymers, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polythioesters, polysulfonamides, polyureas, polyphosphazenes, polysilazanes, and the like, as well as combinations comprising at least one of the foregoing polymers. Preferred polymeric mixtures are those derived from a polycarbonate, polyesters such as cycloaliphatic polyesters and polyarylates, and polycarbonate-polydimethylsiloxane copolymers.

Preferred polymeric mixtures derived from mixing polycarbonate and polyesters are PC-PCCD, PC-PETG, PC-PET, PC-PBT, PC-PCT, PC-PCTG, PC—PPC, PC-PCCD-PETG, PC-PCCD-PCT, PC-PPC-PCTG, PC-PCTG-PETG, PC-polyarylates, and the like, as well as combinations comprising at least one of the foregoing polymeric mixtures.

As stated above, a preferred polymeric mixture is a polycarbonate-cycloaliphatic polyester mixture. As used herein, the terms "polycarbonate", "polycarbonate composition", and "composition comprising aromatic carbonate chain units" includes compositions having structural units of the formula (I):

(I)

in which greater than or equal to about 60 percent of the total number of $R^1$ groups are aromatic organic radicals and the balance thereof are aliphatic, alicyclic, or aromatic radicals. Preferably, $R^1$ is an aromatic organic radical and, more preferably, a radical of the formula (II):

(II)

wherein each of $A^1$ and $A^2$ is a monocyclic divalent aryl radical and $Y^1$ is a bridging radical having zero, one, or two atoms which separate $A^1$ from $A^2$. In an exemplary embodiment, one atom separates $A^1$ from $A^2$. Illustrative, examples of radicals of this type are —O—, —S—, —S(O)—, —S(O$_2$)—, —C(O)—, methylene, cyclohexyl-methylene, 2-[2,2,1]-bicycloheptylidene, ethylidene, isopropylidene, neopentylidene, cyclohexylidene, cyclopentadecylidene, cyclododecylidene, adamantylidene, and the like. In another embodiment, zero atoms separate $A^1$ from $A^2$, with an illustrative example being bisphenol (OH-benzene-benzene-OH). The bridging radical $Y^1$ can be a hydrocarbon group or a saturated hydrocarbon group such as methylene, cyclohexylidene or isopropylidene.

Polycarbonates may be produced by the Schotten-Bauman interfacial reaction of the carbonate precursor with dihydroxy compounds. Generally, an aqueous base such as (e.g., sodium hydroxide, potassium hydroxide, calcium hydroxide, and the like) is mixed with an organic, water immiscible solvent such as benzene, toluene, carbon disulfide, or dichloromethane, which contains the dihydroxy compound. A phase transfer agent is generally used to facilitate the reaction. Molecular weight regulators may be added either singly or in admixture to the reactant mixture. Branching agents, described forthwith may also be added singly or in admixture.

Polycarbonates can be produced by the interfacial reaction of dihydroxy compounds in which only one atom separates $A^1$ and $A^2$. As used herein, the term "dihydroxy compound" includes, for example, bisphenol compounds having general formula (III) as follows:

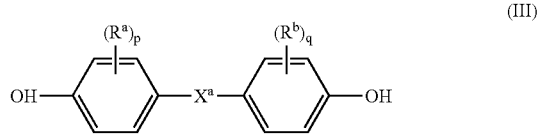

wherein $R^a$ and $R^b$ each independently represent hydrogen, a halogen atom, or a monovalent hydrocarbon group; p and q are each independently integers from 0 to 4; and $X^a$ represents one of the groups of formula (IV):

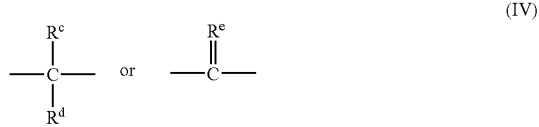

wherein $R^c$ and $R^d$ each independently represent a hydrogen atom or a monovalent linear or cyclic hydrocarbon group, and $R^e$ is a divalent hydrocarbon group.

Examples of the types of bisphenol compounds that may be represented by formula (III) includes the bis(hydroxyaryl)alkane series such as, 1,1-bis(4-hydroxyphenyl)methane, 1,1-bis(4-hydroxyphenyl)ethane, 2,2-bis(4-hydroxyphenyl) propane (or bisphenol-A), 2,2-bis(4-hydroxyphenyl)butane, 2,2-bis(4-hydroxyphenyl)octane, 1,1-bis(4-hydroxyphenyl) propane, 1,1-bis(4-hydroxyphenyl)n-butane, bis(4-hydroxyphenyl)phenylmethane, 2,2-bis(4-hydroxy-1-methylphenyl)propane, 1,1-bis(4-hydroxy-t-butylphenyl)propane, 2,2-bis(4-hydroxy-3-bromophenyl)propane, and the like; bis (hydroxyaryl)cycloalkane series such as, 1,1-bis(4-hydroxyphenyl)cyclopentane, 1,1-bis(4-hydroxyphenyl) cyclohexane, and the like; and the like, as well as combinations comprising at least one of the foregoing bisphenol compounds.

Other bisphenol compounds that may be represented by formula (III) include those where X is —O—, —S—, —SO— or —S(O)$_2$—. Some examples of such bisphenol compounds are bis(hydroxyaryl)ethers such as 4,4'-dihydroxy diphenylether, 4,4'-dihydroxy-3,3'-dimethylphenyl ether, and the like; bis(hydroxy diaryl)sulfides, such as 4,4'-dihydroxy diphenyl sulfide, 4,4'-dihydroxy-3,3'-dimethyl diphenyl sulfide, and the like; bis(hydroxy diaryl) sulfoxides, such as, 4,4'-dihydroxy diphenyl sulfoxides, 4,4'-dihydroxy-3,3'-dimethyl diphenyl sulfoxides, and the like; bis(hydroxy diaryl)sulfones, such as 4,4'-dihydroxy diphenyl sulfone, 4,4'-dihydroxy-3,3'-dimethyl diphenyl sulfone, and the like; and the like, as well as combinations comprising at least one of the foregoing bisphenol compounds.

Other bisphenol compounds that may be utilized in the polycondensation of polycarbonate are represented by the formula (V)

wherein, $R^f$, is a halogen atom of a hydrocarbon group having 1 to 10 carbon atoms or a halogen substituted hydrocarbon group; n is a value from 0 to 4. When n is at least 2, $R^f$ may be the same or different. Examples of bisphenol compounds that may be represented by the formula (V), are resorcinol, substituted resorcinol compounds such as 3-methyl resorcin, 3-ethyl resorcin, 3-propyl resorcin, 3-butyl resorcin, 3-t-butyl resorcin, 3-phenyl resorcin, 3-cumyl resorcin, 2,3,4,6-tetrafloro resorcin, 2,3,4,6-tetrabromo resorcin, and the like; catechol, hydroquinone, substituted hydroquinones, such as 3-methyl hydroquinone, 3-ethyl hydroquinone, 3-propyl hydroquinone, 3-butyl hydroquinone, 3-t-butyl hydroquinone, 3-phenyl hydroquinone, 3-cumyl hydroquinone, 2,3,5,6-tetramethyl hydroquinone, 2,3,5,6-tetra-t-butyl hydroquinone, 2,3,5,6-tetrafloro hydroquinone, 2,3,5,6-tetrabromo hydroquinone, and the like; and the like, as well as combinations comprising at least one of the foregoing bisphenol compounds.

Bisphenol compounds such as 2,2,2',2'-tetrahydro-3,3,3',3'-tetramethyl-1,1'-spirobi-[1H-indene]-6,6'-diol represented by the following formula (VI) may also be used.

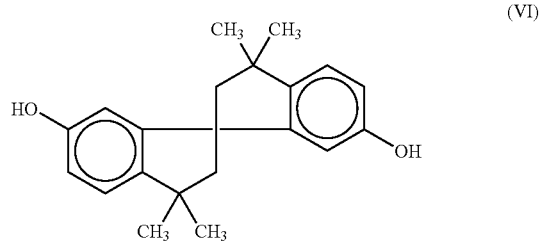

The preferred bisphenol compound is bisphenol A.

Typical carbonate precursors include the carbonyl halides, for example, carbonyl chloride (phosgene), carbonyl bromide, and the like; the bis-haloformates, for example, the bis-haloformates of dihydric phenols such as bisphenol A, hydroquinone, and the like; the bis-haloformates of glycols such as ethylene glycol, neopentyl glycol, and the like; the diaryl carbonates, such as diphenyl carbonate, di(tolyl) carbonate, di(naphthyl) carbonate, and the like; and the like, as well as combinations comprising at least one of the foregoing carbonate precursors. The preferred carbonate precursor for the interfacial reaction is carbonyl chloride.

Branched polycarbonates are also useful, as well as mixtures of linear polycarbonate and a branched polycarbonate. The branched polycarbonates may be prepared by adding a branching agent during polymerization. These branching agents may comprise polyfunctional organic compounds containing at least three functional groups, which may be hydroxyl, carboxyl, carboxylic anhydride, haloformyl, and combinations comprising at least one of the foregoing branching agents. Specific examples include trimellitic acid, trimellitic anhydride, trimellitic trichloride, tris-p-hydroxy phenyl ethane, isatin-bis-phenol, tris-phenol TC (1,3,5-tris ((p-hydroxyphenyl)isopropyl)benzene), tris-phenol PA (4(4 (1,1-bis(p-hydroxyphenyl)-ethyl)α,α-dimethyl benzyl)phenol), 4-chloroformyl phthalic anhydride, trimesic acid, benzophenone tetracarboxylic acid, and the like, as well as combinations comprising at least one of the foregoing branching agents. The branching agents may be added, for example, in an amount of about 0.05 to about 2.0 wt %, based upon the total weight of the polycarbonate.

In one embodiment, the polycarbonate may be produced by a melt polycondensation reaction between a dihydroxy compound and a carbonic acid diester. Examples of the carbonic acid diesters that may be utilized to produce the polycarbonates are diphenyl carbonate, bis(2,4-dichlorophenyl)carbonate, bis(2,4,6-trichlorophenyl)carbonate, bis(2-cyanophenyl)carbonate, bis(o-nitrophenyl)carbonate, ditolyl carbonate, m-cresyl carbonate, dinaphthyl carbonate, bis (diphenyl)carbonate, diethyl carbonate, dimethyl carbonate, dibutyl carbonate, dicyclohexyl carbonate, and the like, as well as combinations comprising at least one of the foregoing carbonic acid diesters. The preferred carbonic acid diester is diphenyl carbonate.

Preferably, the number average molecular weight ($M_n$) of the polycarbonate is about 500 to about 1,000,000 grams/mole (g/mole). Within this range, it is desirable to have a number average molecular weight of greater than or equal to about 1,000 g/mole, preferably greater than or equal to about 5,000 g/mole, and more preferably greater than or equal to about 10,000 g/mole. Also desirable is a number average molecular weight of less than or equal to about 200,000 g/mole, preferably less than or equal to about 100,000 g/mole, more preferably less than or equal to about 65,000 g/mole, and most preferably less than or equal to about 40,000 g/mole. An exemplary number average molecular weight for the polycarbonate is about 9,000 g/mole to about 38,000 g/mole.

Cycloaliphatic polyesters suitable for use in the polymeric mixtures are those that are characterized by optical transparency, improved weatherability, chemical resistance, and low water absorption. It is also generally desirable that the cycloaliphatic polyesters have good melt compatibility with the polycarbonate polymers. Cycloaliphatic polyesters are generally prepared by reaction of a diol with a dibasic acid or derivative. The diols useful in the preparation of the cycloaliphatic polyesters may be straight chain, branched, or cycloaliphatic, preferably straight chain or branched alkane diols, and may contain from 2 to 12 carbon atoms.

Suitable examples of diols include ethylene glycol, propylene glycol such as 1,2- and 1,3-propylene glycol, and the like; butane diol such as 1,3- and 1,4-butane diol, and the like; diethylene glycol, 2,2-dimethyl-1,3-propane diol, 2-ethyl, 2-methyl, 1,3-propane diol, 1,3- and 1,5-pentane diol, dipropylene glycol, 2-methyl-1,5-pentane diol, 1,6-hexane diol, 1,4-cyclohexane dimethanol and particularly its cis- and trans-isomers, triethylene glycol, 1,10-decane diol, and combinations comprising at least one of the foregoing diols. Particularly preferred is dimethanol bicyclo octane, dimethanol decalin, a cycloaliphatic diol or chemical equivalents thereof, and particularly 1,4-cyclohexane dimethanol or its chemical equivalents. If 1,4-cyclohexane dimethanol is to be used as the diol component, it is generally preferred to use a mixture of cis- to trans-isomes in ratios of about 1:4 to about 4:1. Within this range, it is generally desired to use a ratio of cis- to trans-isomers of about 1:3.

The diacids useful in the preparation of the cycloaliphatic polyester polymers are aliphatic diacids that include carboxylic acids having two carboxyl groups each of which are attached to a saturated carbon in a saturated ring. Suitable examples of cycloaliphatic acids include decahydro naphthalene dicarboxylic acid, norbornene dicarboxylic acids, bicyclo octane dicarboxylic acids. Preferred cycloaliphatic diacids are 1,4-cyclohexanedicarboxylic acid and trans-1,4-cyclohexanedicarboxylic acids. Linear aliphatic diacids are also useful provided the polyester has at least one monomer containing a cycloaliphatic ring. Illustrative examples of linear aliphatic diacids are succinic acid, adipic acid, dimethyl succinic acid, azelaic acid, and the like, as well as combinations comprising at least one of the foregoing. Mixtures of diacid and diols may also be used to make the cycloaliphatic polyesters.

Cyclohexanedicarboxylic acids and their chemical equivalents can be prepared, for example, by the hydrogenation of cycloaromatic diacids and corresponding derivatives such as isophthalic acid, terephthalic acid or naphthalenic acid, in a suitable solvent (e.g., water or acetic acid) at room temperature and at atmospheric pressure using catalysts such as rhodium supported on a carrier comprising carbon and alumina. They may also be prepared by the use of an inert liquid medium wherein an acid is at least partially soluble under reaction conditions and a catalyst of palladium or ruthenium in carbon or silica is used.

Generally, during hydrogenation, two or more isomers are obtained in which the carboxylic acid groups are in cis- or trans-positions. The cis- and trans-isomers can be separated by crystallization with or without a solvent, for example, n-heptane, or by distillation. The cis-isomer tends to be more miscible, however, the trans-isomer has higher melting and crystallization temperatures and is especially preferred. Mixtures of the cis- and trans-isomers may also be used, and preferably when such a mixture is used, the trans-isomer will preferably comprise at least about 75 wt % and the cis-isomer will comprise the remainder based on the total weight of cis- and trans-isomers combined. When a mixture of isomers or more than one diacid is used, a copolyester or a mixture of two polyesters may be used as the cycloaliphatic polyester resin.

Chemical equivalents of these diacids including esters may also be used in the preparation of the cycloaliphatic polyesters. Suitable examples of the chemical equivalents of the diacids are alkyl esters, e.g., dialkyl esters, diaryl esters, anhydrides, acid chlorides, acid bromides, and the like, as well as combinations comprising at least one of the foregoing chemical equivalents. The preferred chemical equivalents comprise the dialkyl esters of the cycloaliphatic diacids, and the most preferred chemical equivalent comprises the dimethyl ester of the acid, particularly dimethyl-trans-1,4-cyclohexanedicarboxylate.

Dimethyl-1,4-cyclohexanedicarboxylate can be obtained by ring hydrogenation of dimethylterephthalate, and two isomers having the carboxylic acid groups in the cis- and trans-positions are obtained. The isomers can be separated, the trans-isomer being especially preferred. Mixtures of the isomers may also be used as detailed above.

The polyester polymers are generally obtained through the condensation or ester interchange polymerization of the diol or diol chemical equivalent component with the diacid or diacid chemical equivalent component and having recurring units of the formula (VII):

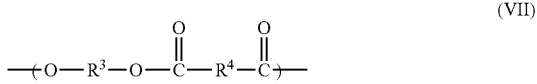

(VII)

wherein R³ represents an alkyl or cycloalkyl radical containing 2 to 12 carbon atoms and which is the residue of a straight chain, branched, or cycloaliphatic alkane diol having 2 to 12 carbon atoms or chemical equivalents thereof; and R⁴ is an alkyl or a cycloaliphatic radical which is the decarboxylated residue derived from a diacid, with the proviso that at least one of R³ or R⁴ is a cycloalkyl group.

A preferred cycloaliphatic polyester is PCCD having recurring units of formula (VIII)

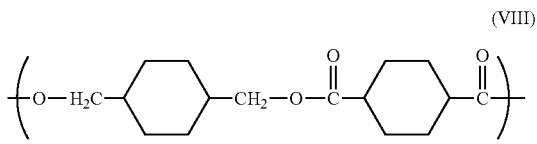

(VIII)

wherein in the formula (VII) R³ is a cyclohexane ring, and wherein R⁴ is a cyclohexane ring derived from cyclohexanedicarboxylate or a chemical equivalent thereof and is selected from the cis- or trans-isomer or a mixture of cis- and trans-isomers thereof. Cycloaliphatic polyester polymers can be generally made in the presence of a suitable catalyst such as a tetra(2-ethyl hexyl)titanate, in a suitable amount, generally about 50 to 400 ppm of titanium based upon the total weight of the final product.

It is generally desirable for the number average molecular weight ($M_n$) of the polyester to be about 500 to about 1,000,000 grams/mole (g/mole). Within this range, it is desirable to have a number average molecular weight of greater than or equal to about 1,000, preferably greater than or equal to about 5,000 g/mole, and more preferably greater than or equal to about 10,000 g/mole. Also desirable is a number average molecular weight of less than or equal to about 200,000, preferably less than or equal to about 100,000, more preferably less than or equal to about 75,000 g/mole, and most preferably less than or equal to about 60,000 g/mole. An exemplary number average molecular weight for the polyester is about 40,000 to about 55,000 g/mole.

PCCD generally forms suitable mixtures with the polycarbonate. It is generally desirable for a polycarbonate-PCCD mixture to have a melt volume rate of greater than or equal to about 5 cubic centimeters/10 minutes (cc/10 min or ml/10 min) to less than or equal to about 150 cubic centimeters/10 minutes when measured at 265° C., at a load of 2.16 kilograms and a four minute dwell time. Within this range, it is generally desirable to have a melt volume rate of greater than or equal to about 7, preferably greater than or equal to about 9, and more preferably greater than or equal to about 10 cc/10 min when measured at 265° C., at a load of 2.16 kilograms and a four minute dwell time. Also desirable within this range, is a melt volume rate of less than or equal to about 125, preferably less than or equal to about 110, and more preferably less than or equal to about 100 cc/10 minutes.

In general, it is desirable for the polycarbonate-PCCD mixture to have a glass transition temperature of less than or equal to about 205° C., preferably less than or equal to about 175° C., and more preferably less than or equal to about 150° C., and most preferably less than or equal to about 95° C.

Another preferred polyester that may be mixed with other polymers are polyarylates. Polyarylates generally refers to polyesters of aromatic dicarboxylic acids and bisphenols. Polyarylate copolymers that include carbonate linkages in addition to the aryl ester linkages, are termed polyester-carbonates, and may also be advantageously utilized in the mixtures. The polyarylates can be prepared in solution or by the melt polymerization of aromatic dicarboxylic acids or their ester forming derivatives with bisphenols or their derivatives.

In general, it is preferred for the polyarylates to comprise at least one diphenol residue in combination with at least one aromatic dicarboxylic acid residue. The preferred diphenol residue, illustrated in formula (IX), is derived from a 1,3-dihydroxybenzene moiety, referred to throughout this specification as resorcinol or resorcinol moiety. Resorcinol or resorcinol moieties include both unsubstituted 1,3-dihydroxybenzene and substituted 1,3-dihydroxybenzenes.

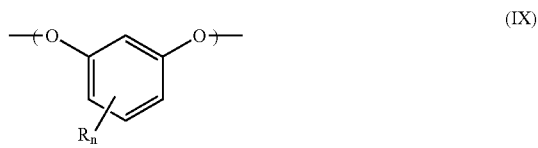

(IX)

In formula (IX), R is at least one of $C_{1-12}$ alkyl or halogen, and n is 0 to 3. Suitable dicarboxylic acid residues include aromatic dicarboxylic acid residues derived from monocyclic moieties, preferably isophthalic acid, terephthalic acid, or mixtures of isophthalic and terephthalic acids, or from polycyclic moieties such as diphenyl dicarboxylic acid, diphenylether dicarboxylic acid, and naphthalene-2,6-dicarboxylic acid, and the like, as well as combinations comprising at least one of the foregoing polycyclic moieties. The preferred polycyclic moiety is naphthalene-2,6-dicarboxylic acid.

Preferably, the aromatic dicarboxylic acid residues are derived from mixtures of isophthalic and/or terephthalic acids as generally illustrated in formula (X).

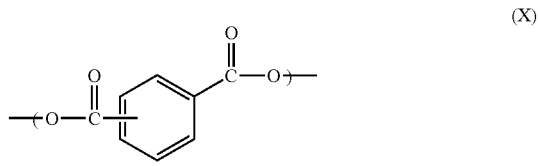

(X)

therefore, on one embodiment the polyarylates comprise resorcinol arylate polyesters as illustrated in formula (XI) wherein R and n are previously defined for formula (IX).

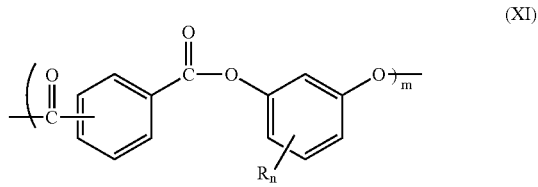

(XI)

wherein R is at least one of $C_{1-12}$ alkyl or halogen, n is 0 to 3, and m is at least about 8. It is preferred for R to be hydrogen. Preferably, n is zero and m is about 10 and about 300. The molar ratio of isophthalate to terephthalate is about 0.25:1 to about 4.0:1.

In another embodiment, the polyarylate comprises thermally stable resorcinol arylate polyesters that have polycyclic aromatic radicals as shown in formula (XII)

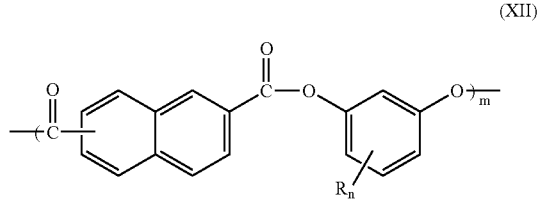

(XII)

wherein R is at least one of $C_{1-12}$ alkyl or halogen, n is 0 to 3, and m is at least about 8.

In another embodiment, the polyarylates are copolymerized to form block copolyestercarbonates, which comprise carbonate and arylate blocks. They include polymers comprising structural units of the formula (XIII)

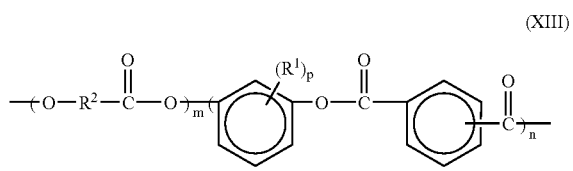

(XIII)

wherein each $R^1$ is independently halogen or $C_{1-12}$ alkyl, m is at least 1, p is about 0 to about 3, each $R^2$ is independently a divalent organic radical, and n is at least about 4. Preferably n is at least about 10, more preferably at least about 20 and most preferably about 30 to about 150. Preferably m is at least about 3, more preferably at least about 10 and most preferably about 20 to about 200. In an exemplary embodiment m is present in an amount of about 20 and 50.

Yet another preferred thermoplastic polymer is a copolymer of polycarbonate and polysiloxane. The polysiloxane polymer used in the copolymer generally has a viscosity of about 100 to 1,000,000 poise at 25° C. and has chain substituents selected from the group comprising of hydride, methyl, ethyl, propyl, vinyl, phenyl, and trifluoropropyl. The end groups on the polysiloxane polymer may be hydride, hydroxyl, vinyl, vinyl diorganosiloxy, alkoxy, acyloxy, allyl, oxime, aminoxy, isopropenoxy, epoxy, mercapto groups, or other known, reactive end groups.

The thermoplastic polymers may be mixed in any desired suitable ratios to form the polymeric mixture. Binary mixtures, ternary mixtures and mixtures having more than three polymers may also be used in the polymeric mixtures. When a binary mixture or ternary mixture is used in the polymeric mixture, one of the polymers in the mixture may comprise about 1 to about 99 weight percent (wt %) based on the total weight of the composition. Within this range, it is generally desirable to have the one of the polymers in an amount greater than or equal to about 20 wt %, preferably greater than or equal to about 30 wt % and more preferably greater than or equal to about 35 wt %, based on the total weight of the composition. Also desirable within this range, is an amount of less than or equal to about 90 wt %, preferably less than or equal to about 80 wt %, and more preferably less than or equal to about 70 wt % based on the total weight of the composition. A preferred mixture comprises 60 wt % polycarbonate and 40 wt % PCCD. When ternary mixtures having more than three polymers are used, the various polymers may be present in any desirable weight ratio.

In order to manufacture the appliance, it is generally desirable to shape the mixture into a sheet. The sheets used in the manufacture of the appliance may be of a uniform thickness or of a variable thickness. When the sheet generally has a uniform thickness prior to being formed into the appliance, it is to be noted that the sheet thickness will generally vary after being formed into the appliance. The thickness of the sheet is generally selected to provide for ease of repositioning as well as for ease of comfort. The sheet may have a thickness of about 125 (5 mils) to about 1,250 (50 mils) micrometers. Within this range, a thickness of greater than or equal to about 200 micrometers, preferably greater than or equal to about 350 micrometers, more preferably greater than or equal to about 400 micrometers may be used. Also desirable within this range, is a thickness of less than or equal to about 1,000 micrometers, preferably less than or equal to about 950 micrometers and more preferably less than or equal to about 875 micrometers. An exemplary thickness is about 700 micrometers to about 800 micrometers.

It is generally desirable for the polymeric mixture to have a tensile strength and modulus effective to reposition the teeth in the oral cavity over a period of time. The tensile modulus of the material should be adjusted so that the appliance can be installed and removed without causing damage to the patient's oral cavity. It is preferred for the polymeric mixture to have an elastic modulus of about 1,500 Newton/square millimeter ($N/mm^2$) to about 2,500 $N/mm^2$ when measured in tensile deformation at a rate of 2 millimeters/minute at room temperature prior to insertion in the oral cavity. In general, a tensile strength of greater than or equal to about 1,600 $N/mm^2$, preferably greater than or equal to about 1,650 $N/mm^2$, and more preferably greater than or equal to about 1,700 $N/mm^2$ is suitable.

It is also generally desirable for the polymeric mixture to display stress retention for purposes of successfully repositioning the teeth in the oral cavity. It is generally desirable for the polymeric mixture to have a percent stress retention of greater than or equal to about 50%, preferably greater than or equal to about 60%, more preferably greater than or equal to about 70%, and even more preferably greater than or equal to about 75% of the applied stress, when stressed for a period of 12 hours, prior to use in the oral cavity.

It is also desirable for the polymeric mixture to be stain resistant. Stain resistance is desirable for cosmetic and aesthetic reasons. Stain resistance is expressed as Delta E and is the difference in color prior to immersion in a staining agent (e.g., coffee, wine, tomato sauces, and the like) and after immersion in a staining agent followed by the washing of the mixture in a detergent. It is generally desirable to have a Delta E of less than or equal to about 2, preferably less than or equal to about 1.5, more preferably less than or equal to about 1.0, and even more preferably less than or equal to about 0.75.

It is further desirable for the polymeric mixture to have a yellowness index of less than or equal to about 1 and a percent haziness of less than or equal to about 0.5 prior to use in the oral cavity. Within the range for yellowness index, it is generally desirable to have a value of less than or equal to about 0.8, preferably less than or equal to about 0.7, and more preferably less than or equal to about 0.6, while having a haze of less than 0.45, preferably less than or equal to about 0.42, and more preferably less than or equal to about 0.4, when the sheet has a thickness of up to about 500 micrometers. An exemplary value of yellowness index is about 0.35 to about 0.45 and an exemplary value of haze is about 0.23 to about 0.3 prior to introduction into the oral cavity.

While it is generally desirable for the mixture to be transparent, it may also be opaque if desired. A patient may use opaque appliances after dark, when the appearance of the appliance is not of paramount importance. In addition, opaque appliances may be worn by patients during periods of sleep, when the appliance is not likely to be noticed.

In one embodiment, the appliance may comprise additional layers disposed upon the sheet comprising the polymeric mixture. The additional layers may comprise a first layer disposed upon a surface of the sheet comprising the polymeric mixture, and an optional second layer disposed upon a surface of the sheet opposite the surface in contact with the first layer. The additional layers generally comprise an organic polymer having a tensile modulus of less than or equal to about 1,000 N/mm$^2$. Preferred organic polymers for the additional layers are elastomers. Suitable examples of elastomers for the first layer and/or second layer include silicones, fluoroelastomers, styrene-butadienes, styrene-isoprenes, polybutadienes, polyisobutylenes, polyurethanes, chlorosulfonates, butyls, neoprenes, nitrites, polyisoprenes, plasticized nylons, polyesters, polyvinyl ethers, polyvinyl acetates, polyisobutylenes, ethylene vinyl acetates, copolyester ethers, polyolefins, and polyvinyl chlorides, copolymer rubbers such as ethylene-propylene (EPR), ethylene-propylene-diene monomer (EPDM), copolyester ethers, styrene-isoprene-styrene (SIS), styrene-butadiene-styrene (SBS), nitrile-butadienes (NBR) and styrene-butadienes (SBR), mixtures such as ethylene propylene diene monomer (EPDM), EPR, or NBR, and mixtures and copolymers thereof. A preferred elastomer for the first layer is a copolyester ether. Another preferred organic polymer for the first layer and/or second layer is PCCD. When the appliance comprises only one additional layer, (e.g., a first layer), it is generally desirable to place the appliance in the mouth of the patient in such a manner so that the first layer contacts the gums of the patient. Since the first layer generally comprises a softer material than the polymeric mixture it can be used effectively to alleviate pain, discomfort and bleeding gums. A preferred elastomer is ECDEL 9966 commercially available from Eastman Chemical Company at Kingsport, Tenn.

In one embodiment, the polymeric mixture and/or the elastomer may contain additives such as mold release agents, pigments, dyes, impact modifiers, lubricants, anti-oxidants, anti-ozonants, anti-microbials, flame retardants, visual effect additives, fibers, nanotubes, antistatic agents, plasticizers, fillers, and the like, as well as combinations of one of the foregoing additives.

In certain applications it may be desirable to add fibers to the polymeric mixture. The fibers may be in the form of whiskers, needles, rods, tubes, strands, elongated platelets, lamellar platelets, ellipsoids, micro fibers, nanofibers and nanotubes, elongated fullerenes, and the like, as well as combinations comprising at least one of the foregoing. The fibers may also include short inorganic fibers, mineral fibers single crystal fibers, metal fibers, textile glass fibers and the like, as well as combinations comprising at least one of the foregoing fibers.

Also included are natural organic fibers such as, for example, wood flour obtained by pulverizing wood, and fibrous products such as cellulose, cotton, sisal, jute, cloth, hemp cloth, felt, and natural cellulosic fabrics such as Kraft paper, cotton paper and glass fiber containing paper, starch, cork flour, lignin, ground nut shells, corn, rice grain husks, and the like, as well as combinations comprising at least one of the foregoing.

Synthetic reinforcing fibers such as, for example, fibers manufactured from polyethylene terephthalate, polybutylene terephthalate and other polyesters, polyarylates, polyethylene, polyvinylalcohol, polytetrafluoroethylene, acrylic resins, aromatic polyamides, polyaramids, polybenzimidazoles, polyphenylene sulfides, polyether ether ketone, polybenzoxazoles, aromatic polyimides, polyetherimides, and the like, as well as combinations comprising at least one of the foregoing reinforcing fibers may also be incorporated into the polymeric mixture.

Fibers may be provided in the form of monofilament or multifilament fibers and can be used either alone or in combination with other types of fiber, through, for example, co-weaving, core/sheath, side-by-side, orange-type or matrix and fibril constructions, or by other methods used in fiber manufacture. Typical cowoven structures include glass fiber-carbon fiber, carbon fiber-aromatic polyimide fiber, and aromatic polyimide fiber-glass fiber. Fibers may be supplied in the form of, for example, rovings, woven fibrous reinforcements, such as 0 to 90 degree fabrics, non-woven fibrous reinforcements such as continuous strand mat, chopped strand mat, tissues, papers, felts and 3-dimensionally woven reinforcements, performs and braids.

In general, the amount of fibrous filler present in the polymeric mixture can be up to about 50 wt %, based on the total weight of the polymeric mixture. Within this range, it is generally desirable to have fibrous fillers present in amounts of greater than or equal to about 2 wt %, preferably greater than or equal to about 5 wt %, preferably greater than or equal to about 10 wt %, and more preferably greater than or equal to about 20 wt %, based on the total weight of the polymeric mixture.

In order to make a suitable appliance for repositioning the teeth, it is generally desirable to have the polymeric mixture in the form of a sheet. A polymeric mixture may generally be formed into a sheet by mixing the polymers in a device that can impart shear to the polymers. Suitable devices are extruders such as single and twin-screw extruders, Buss kneaders, roll mills, helicones, and the like. It may be desirable to couple a twin screw extruder with a single screw extruder to mix the polymers prior to calendaring the mixture in a roll mill. The calendaring of the mixture facilitates the production of the sheet. In one embodiment, it is generally desirable to form the sheet on a roll mill wherein the mating surfaces of the rolls are both polished. Such a sheet is termed a polish/polish sheet. Sheets having a matte/polish finish may also be used. After the manufacture of the sheet, it may be formed into an appliance for repositioning the teeth as detailed below. The forming of the appliance may be accomplished by process such as thermoforming, molding, and the like, which are discussed in detail below.

FIG. 2 is a schematic depicting the procedure by which the appliances may be manufactured in order to effect the repositioning of the teeth. As a first step, an initial digital data set (IDDS) representing the initial tooth arrangement is obtained. The IDDS may be obtained in a variety of ways. For example, the patient's teeth may be scanned or imaged using methods such as x-rays, three-dimensional x-rays, computer-aided tomographic images or data sets, magnetic resonance images, and the like, as well as combinations comprising at least one of the foregoing methods. The IDDS may also be made after first obtaining a plaster cast of the patient's teeth. After the plaster cast is obtained, it can be digitally scanned using a laser scanner or another range acquisition system to produce the IDDS. The data set obtained by the range acquisition system may be converted to other formats so as to be compatible with the software which is used for manipulating images within the data set, as described in more detail below.

There are a variety of range acquisition systems, generally categorized by whether the process of acquisition requires contact with the three-dimensional plaster cast. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radiation or sonar. Others utilize optical energy. These non-contact-type systems working by reflected optical energy further contain special instrumentation configured to permit certain measuring techniques to be performed (e.g., imaging radar, triangulation and interferometry).

A preferred range acquisition system is an optical or laser based optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif. Either non-contact-type or contact-type scanners may also include a color camera, that when synchronized with the scanning capabilities, provides a means for capturing, in digital format, a color representation of the plaster cast.

In one embodiment, multiple dental images having incrementally differing geometries may be produced by non-computer-aided techniques. For example, plaster casts obtained as detailed above, may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described below, using pressure and vacuum forming techniques.

In another embodiment, the manipulation of the IDDS may be accomplished at a computer or workstation having a suitable graphical user interface (GUI) and software appropriate for viewing and modifying the images. In this approach, individual teeth and other components will be "cut" to permit their individual repositioning or removal from the digital data. Additional data, such as patient clinical data, geometrical condition of the teeth, material properties relating to the appliances, may be input into a computer algorithm for facilitating repositioning of the teeth. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement is incorporated into a final digital data set (FDDS). The IDDS and the FDDS may then be used to generate a plurality of intermediate digital data sets (INTDDS's). The INTDDS's are generated to correspond to successive intermediate tooth arrangements. A system of incremental position adjustment appliances can then be fabricated based on the INTDDS's, as described below. In general, it is desirable for the system to contain at least one or more INTDDS's, preferably 2 or more INTDDS's, more preferably 10 or more INTDDS's, and more preferably 25 or more INTDDS's.

Once the intermediate and final data sets have been created, the appliances may be fabricated as illustrated in FIG. 3. Preferably, fabrication methods will employ a rapid prototyping device 200 such as a stereolithography machine. A particularly suitable rapid prototyping machine is Model SLA-250/50, commercially available from 3D System, Valencia, Calif. The prototyping machine 200 will receive the individual digital data sets and produce one structure corresponding to each of the desired appliances. As stated above, the appliances are produced from the polymeric mixture.

The rapid prototyping machine 200 may alternatively be used to produce molds, which are, in effect, positive tooth models (replicas) of each successive stage of the treatment. The positive tooth models may then be used to produce the appliance. The positive tooth models are generally made from plaster, epoxy, and the like. The appliance is generally manufactured by processes such as injection molding, compression molding, vacuum forming, blow molding, and the like. Suitable forming equipment is available under the tradename BIOSTAR from Great Lakes Orthodontics, Ltd., Tonawanda, N.Y. The forming machine 250 produces each of the appliances directly from the positive tooth model and the desired material. Suitable vacuum forming machines are available from Raintree Essix, Inc. Metairie, La. These machines may operated in a batch or a continuous fashion.

The thermoforming of the appliance from the sheet is generally carried out at a surface temperature of about 120° C. to about 180° C. The surface temperature referred to herein is the temperature at the surface of the sheet during the forming process. Within this range it is generally desirable to use temperatures of greater than or equal to about 125° C., preferably greater than or equal to about 128° C., and more preferably greater than or equal to about 130° C. Also desirable within this range are temperatures of less than or equal to about 178° C., preferably less than or equal to about 175° C., and more preferably less than or equal to about 170° C. An exemplary thermoforming temperature is about 135° C. to about 150° C.

It is generally desirable to complete the thermoforming in as short a time as possible to improve efficiency of the manufacturing process. The time period for thermoforming a single appliance is about 5 seconds to about 40 seconds. Within this range, it is generally desirable to thermoform an appliance for greater than or equal to about 7 seconds, preferably greater than or equal to about 10 seconds, and more preferably greater than or equal to about 12 seconds. Also desirable within this range is a time period of less than or equal to about 38 seconds, preferably less than or equal to about 34 seconds, and more preferably less than or equal to about 30 seconds.

After manufacturing, the plurality of appliances is preferably supplied to the treating professional all at one time. The appliances will be marked in some manner, generally by sequential numbering directly on the appliances or on tags, pouches, or other items which are affixed to or which enclose each appliance, to indicate their order of use. The appliances are utilized in such a manner to reposition the patient's teeth progressively toward the final tooth arrangement.

The appliance provides a number of advantages over braces. It is aesthetically pleasing and does not undergo any staining while in the mouth. In general, no wires or other means will be provided for holding the appliance in place over the teeth. In some cases, however, it will be desirable to provide individual anchors on teeth with corresponding receptacles or apertures in the appliance 100 so that the appliance can apply an upward force on the tooth that would not be possible in the absence of such an anchor.

The following examples, which are meant to be exemplary, not limiting, illustrate compositions and methods of manufacturing some of the various embodiments of the appliances using various materials and apparatus.

EXAMPLES

Example 1

This example was undertaken to compare the properties of a polycarbonate-PCCD mixture with the properties of the constituent polymers, polycarbonate and PCCD, respectively. The polycarbonate used was PC100 commercially available from GE Plastics. Two types of PCCD were used, PCCD4000 having a number average molecular weight ($M_n$) of 47,000 g/mole and PCCD6000 having a number average molecular weight of 51,500 g/mole. The polycarbonate and the PCCD were first mixed in a 50:50 or a 60:40 weight ratio in a 92 millimeter (mm) Werner and Pfleiderer (megacompounder) twin screw extruder. The PC100 sample is designated Comparative Sample #1, while the PCCD4000 and PCCD6000 samples have been designated Comparative Sample #2 and Comparative Sample #3 respectively. The sample containing the polycarbonate and PCCD in the 50:50 weight ratio is designated Sample #4, while the sample containing the polycarbonate and PCCD in the 60:40 weight ratio is designated Sample #5.

A quencher comprising phosphoric acid was used to minimize any reaction between the polycarbonate and the PCCD. A radical scavenger comprising phosphonous acid ester was added to the mixture. No UV inhibitors were used in these examples. The mixture was first pelletized and dried at a temperature of about 82° C. (180° F.) for 6 hours. The dried pellets were then extruded in a single screw extruder having a 4.5 inch (11.43 centimeters) screw diameter. The single screw extruder was a single stage, barrier type extruder with a length to diameter ratio (L/D) of 24:1 and with a flex lip die. The extrusion conditions are shown in Table 1.

TABLE 1

| Parameter | Value |
| --- | --- |
| Extruder diameter (inches) | 4.5 |
| Drying temperature (° C.) | 82.22 |
| Drying Time (hours) | 6 |
| Extruder Temperatures (° C.) | Pre-set |
| Zone 1 (° C.) | 207.22 |
| Zone 2 (° C.) | 215.56 |
| Zone 3 (° C.) | 221.67 |
| Zone 4 (° C.) | 235.00 |
| Zone 5 (° C.) | 252.22 |
| Adapter Temperature (° C.) | 243.33 |
| Die Lips Temperature (° C.) | 252.78 |
| Screw RPM | 24.3 |
| Extruder Amps | 212 |
| Screen mesh | 105 |
| Roll Stack Temperature (° C.) | 26/90 |
| Roll #3 Temperature (° C.) | 148.9 |
| Production speed (feet/min) | 7.6 |

The extrudate from the single screw extruder was fed into a 3-roll, cooled roll stack for purposes of calendaring into a film. The roll stack had one oil cooled roll having an outer sleeve of silicon based rubber and one highly polished oil cooled roll. The sheet emerging from the roll stack was a matt/polish sheet having a thickness of 750 micrometers (30 mils).

The sheet thus obtained was then subjected to a tensile test as per ASTM D 882 in an instron at a rate of 50 mm/minute at room temperature to determine the tensile modulus, tensile strength, and elongation at yield. The results of these tests are shown in Table 2.

TABLE 2

| | Comparative Sample 1 | Comparative Sample 2 | Comparative Sample 3 | Sample 4 | Sample 5 |
| --- | --- | --- | --- | --- | --- |
| Resin | PC100 | PCCD4000 | PCCD6000 | PC/PCCD (50/50) | PC/PCCD (60/40) |
| Tensile Modulus (N/mm²) | 1743.94 | 1046.12 | 1027.80 | 1612.44 | 1748.11 |
| Tensile Strength at Yield (N/mm²) | 57.72 | 34.21 | 33.75 | 47.54 | 52.91 |
| Elongation at Yield (%) | 6.95 | 3.84 | 3.94 | 4.66 | 5.60 |
| Tensile Strength at Break (N/mm²) | 63.53 | 37.89 | 36.92 | 51.23 | 56.80 |
| Elongation at Break (%) | 69.14 | 269.61 | 237.82 | 122.24 | 107.95 |

From the Table 2 it may be seen that the Samples 4 and 5 have comparable tensile properties with the polycarbonate resin of Comparative Sample 1. The tensile properties of the Samples 4 and 5 are superior to Comparative Samples 2 and 3, which were made from PCCD.

The samples were then subjected to thermal tests to determine the thermoforming performance of the materials. The glass transition temperature ($T_g$) was measured in a Dynamic Mechanical Analyzer manufactured by TA Instruments. The rate of temperature change was 3° C./minute and the frequency applied was 1 hertz (Hz).

The results are shown in Table 3.

TABLE 3

|  | Comparative Sample 1 | Comparative Sample 2 | Comparative Sample 3 | Sample 4 | Sample 5 |
| --- | --- | --- | --- | --- | --- |
| Resin | PC100 | PCCD4000 | PCCD6000 | PC/PCCD (50/50) | PC/PCCD (60/40) |
| Tg (° C.) | 145.00 | 65.00 | 65.00 | 111.00 | 120.00 |
| Power heaters (%)* | 100.00 | 70.00 | 70.00 | 100.00 | 100.00 |
| Forming temperature (° C.) | 203.00 | 195.00 | 193.00 | 180.00 | 180.00 |
| Heating time (seconds) | 35.00 | 40.00 | 45.00 | 20.00 | 20.00 |
| Cooling time (seconds) | 10.00 | 40.00 | 40.00 | 10.00 | 10.00 |
| Visual Observations | Excellent part/ homogenous distribution | Acceptable part/ hazy sample | Acceptable part/ hazy sample | Excellent part/ homogenous distribution/ optical performance is excellent | Excellent part/ homogenous distribution/ optical performance is excellent |

*indicates the wattages consumed in performing the heating experiment.

Table 3 shows that the mixtures of Samples 4 and 5 have higher glass transition temperatures than Comparative Samples 2 and 3. In addition, the thermoforming temperature for the mixtures of Samples 4 and 5 is 23° C. lower than the thermoforming temperature of the Comparative Sample 1, which contains only polycarbonate. Lower thermoforming temperatures are advantageous when the sheet is to be deformed over dental mold material. The lower thermoforming temperature reduces fitting corrections due the difference in the coefficient of thermal expansion of the material of the appliance and the mold material. This also improves dimensional stability and insures a good and easy fit to patient's teeth.

The sheets were also subjected to stress relaxation tests using a 1% constant strain in a flexural mode. The stress relaxation test was conducted to determine the force retention of the sheets. This percent force retention provides information about the resiliency of the material that facilitates the repositioning of the tooth during treatment. These stress relaxation tests were conducted in a DMA 2980 (commercially available from TA Instruments, New Castle, Del.) for a time period of 3 hours or 12 hours. The percentage of stress relaxation is measured by the ratio of stress in the sheet at 3 hours or 12 hours to the original stress generated in the sheet upon the application of the 1% constant strain. The results are shown in Table 4.

TABLE 4

|  | Comparative Sample 1 | Comparative Sample 2 | Comparative Sample 3 | Sample 4 | Sample 5 |
| --- | --- | --- | --- | --- | --- |
| Resin | PC100 | PCCD4000 | PCCD6000 | PC/PCCD (50/50) | PC/PCCD (60/40) |
| Stress Relaxation (% Force Retention) after 3 hr | 85 | 43 | 27 | 76 | 80 |
| Stress Relaxation (% Force Retention) after 12 hr | 79 | 31 | 14 | 67 | 73 |

From the Table 4 it may be seen that the percent force retention displayed by the Sample 4 and 5 are similar to those of Comparative Sample 1. The force retention demonstrated by the samples is also sufficient to engineer a specific stress relaxation profile for clinical treatments that may be used to facilitate repositioning the teeth in difficult cases involving missing teeth, deteriorated gums and the like, while at the same time improving clinical treatment efficacy and patient comfort.

The sheets were also subjected to color and optical property tests to determine the aesthetic appearance of the appliance when applied in a patient's oral cavity (i.e., mouth) to reposition the teeth. The color was measured on a MacBeth 7000A using a reflection mode with a white calibration tile as the background. The test was performed as per ASTM D 1003. The observer angle was 10 and 65 degrees respectively. The results are shown in Table 5.

TABLE 5

|  | Comparative Sample 1 | Comparative Sample 2 | Comparative Sample 3 | Sample 4 | Sample 5 |
|---|---|---|---|---|---|
| Resin | PC100 | PCCD4000 | PCCD6000 | PC/PCCD (50/50) | PC/PCCD (60/40) |
| Illume | D65 | D65 | D65 | D66 | D67 |
| L* | 95.61 | 95.43 | 95.42 | 95.21 | 95.22 |
| a* | −0.44 | −0.44 | −0.45 | −0.38 | −0.39 |
| b* | 1.80 | 2.29 | 2.47 | 1.51 | 1.52 |
| % LT (Transmissivity) | 91.70 | 93.17 | 93.07 | 92.00 | 91.77 |
| % Haziness | 0.15 | 0.31 | 0.19 | 0.31 | 0.26 |
| Yellowness Index | 0.60 | 0.70 | 0.80 | 0.10 | 0.40 |

L* = extent of lightness;
a* = extent of redness;
b* = extent of yellowness

From the Table 5, it may seen that the yellowness index for the Sample 4 and 5 are surprisingly better than Comparative Samples 1, 2 and 3. A lower yellowness index indicates a reduced tendency to undergo yellowing, and this makes the appliance aesthetically pleasing.

The sheets were also subjected to staining tests to determine the stain resistance properties. It is generally desirable to use sheets that display a reduced ability to undergo staining upon exposure to a variety of edibles (e.g., food and drink). The staining agents were EZ Brew coffee using a normal brewing cycle and "Ragu, Old World Style, Traditional" tomato sauce. The samples were tested as follows. At least 2 inches (5.1 centimeters) of a 3 inch (7.5 centimeters) strip of sample was immersed in the staining agents at a temperature of 37° C. for 3 days. The results were reproduced three times for each sample and the results were averaged. The samples were placed at least 0.25 inch (0.6 centimeters) apart. The color was measured on the samples before the immersion in the staining agent and again after removal from the container having the staining agent. The exposed samples were washed with water and a mild detergent (e.g., Dawn) prior to drying and making the measurements. The results are shown in the Table 6.

TABLE 6

|  | Comparative Sample 1 | Comparative Sample 2 | Comparative Sample 3 | Sample 4 | Sample 5 |
|---|---|---|---|---|---|
| Resin | PC100 | PCCD4000 | PCCD6000 | PC/PCCD (50/50) | PC/PCCD (60/40) |
| Coffee Delta E | 0.17 | 1.67 | 0.32 | 0.17 | 0.21 |
| Ragu Delta E | 0.05 | 1.87 | 1.93 | 0.17 | 0.09 |

Table 6 shows the Delta E for each sample subjected to the staining agent. The Delta E reflects the difference in color between the measurements made on a sample prior to staining and after washing with the detergent. A high value of Delta E reflects a strong ability to retain stains. From Table 6, it maybe seen that Samples 4 and 5 show very little effects of staining when compared with the Comparative Samples 2 and 3. The Samples 4 and 5 show similar values to the Comparative Sample 1. These low values of stain retention make the mixture very useful for use in the appliances since the presence of stains on any device inserted into the oral cavity is aesthetically unpleasing.

The aforementioned example shows that an mixture of polycarbonate and PCCD in a weight ratio of 50:50 or 60:40 may be advantageously used as an appliance for repositioning teeth since the mixture possesses a unique combination of desirable properties such as a tensile strength of greater than or equal to about 1,500 N/mm$^2$, a stain resistance Delta E of less than or equal to about 2, thermoformability temperatures of less than or equal to about 130° C., and a high percent force retention of greater than or equal to about 60%. This combination of properties makes the polycarbonate-PCCD mixture very useful for dental applications where the unique combination of tensile strength, force retention capabilities, and stain resistance enable an appliance manufactured from the mixture to reposition teeth while at the same time being aesthetically and cosmetically pleasing.

Example 2

This example was undertaken to demonstrate how polycarbonate-PCCD mixtures having different molecular weights have advantageous properties that make them useful for appliances that may be used for repositioning teeth. The number average molecular weights for the respective polycarbonate and PCCD components used in the mixtures are shown in the Table 7. The samples of the individual polycarbonate and PCCD components were extruded in the manner detailed in Example 1. However the extrudate was then injection molded into dogbone samples and subjected to tensile tests in the same manner as detailed in Example 1. These results are also shown in Table 7.

TABLE 7

| Composition | $M_n$ (g/mole) | Tensile Modulus (psi) | Elongation at yield (%) | Elongation at break (%) |
|---|---|---|---|---|
| PC-1 | 9,000 | 2303 | 7.0 | 135 |
| PC-2 | 12,500 | 2303 | 7.0 | 135 |
| PC-3 | 15,000 | 2303 | 7.0 | 110 |
| PCCD-2 | 47,000 | 986 | 4.8 | 215 |
| PCCD-3 | 51,000 | 993 | 4.8 | 215 |

The results shown in the Table 7 demonstrate that while tensile modulus and elongation at yield do not vary much with the molecular weight of the polycarbonate and the PCCD, the elongation at break for the polycarbonate is susceptible to a change in the molecular weight between 12,500 and 15,000 grams/mole (g/mole).

The polycarbonate and the PCCD components of the Table 7 were mixed in extruders in weight ratios of 50:50, 60:40 and 70:30 respectively, in the manner detailed in Example 1. The samples were then injection molded into test specimens. Phosphonous acid ester and phosphoric acid (10 wt % solution in water) were added to the mixture during the extrusion. The compositions are shown in Table 8.

TABLE 8

| Composition | A | B | C |
|---|---|---|---|
| PC-1 or PC-2 or PC-3 (wt %) | 69.8 | 59.8 | 49.8 |
| PCCD-2 or PCCD-3 (wt %) | 29.9 | 39.9 | 49.8 |
| Phosphonous acid ester (PEPQ) (wt %) | 0.1 | 0.1 | 0.1 |
| Phosphoric acid (10% sol. in water) (wt %) | 0.225 | 0.225 | 0.225 |

The resulting molded samples were subjected to tensile tests as per ASTM D 638. The results of these tests are shown in Table 9.

TABLE 9

| PC/PCCD ratio | PC-type | PCCD-type | Modulus (N/mm$^2$) | Elongation at Yield (%) | Elongation at break (%) |
|---|---|---|---|---|---|
| 50/50 | PC-1 | PCCD-2 | 1625.6 | 5.70 | 160.42 |
| 50/50 | PC-1 | PCCD-3 | 1637.8 | 5.70 | 160.42 |
| 50/50 | PC-2 | PCCD-2 | 1618.4 | 5.68 | 160.42 |
| 50/50 | PC-2 | PCCD-3 | 1630.6 | 5.68 | 160.42 |
| 50/50 | PC-3 | PCCD-2 | 1619.2 | 5.82 | 167.33 |
| 50/50 | PC-3 | PCCD-3 | 1623.6 | 5.82 | 165.30 |
| 60/40 | PC-1 | PCCD-2 | 1743.9 | 6.00 | 148.42 |
| 60/40 | PC-1 | PCCD-3 | 1756.0 | 6.00 | 148.42 |
| 60/40 | PC-2 | PCCD-2 | 1762.2 | 5.82 | 148.42 |
| 60/40 | PC-2 | PCCD-3 | 1774.4 | 5.82 | 148.42 |
| 60/40 | PC-3 | PCCD-2 | 1756.3 | 6.00 | 152.19 |
| 60/40 | PC-3 | PCCD-3 | 1760.7 | 6.00 | 151.28 |
| 70/30 | PC-1 | PCCD-2 | 1862.1 | 6.30 | 136.42 |
| 70/30 | PC-1 | PCCD-3 | 1874.3 | 6.30 | 136.42 |
| 70/30 | PC-2 | PCCD-2 | 1906.0 | 5.96 | 136.42 |
| 70/30 | PC-2 | PCCD-3 | 1918.1 | 5.96 | 136.42 |
| 70/30 | PC-3 | PCCD-2 | 1893.4 | 6.18 | 137.04 |
| 70/30 | PC-3 | PCCD-3 | 1897.9 | 6.18 | 137.25 |

From the Table 9, it may be seen that while an increase in the polycarbonate increases the elastic modulus, an increase in the PCCD content increases the elongation at break.

The glass transition temperature for the molded samples was also determined since it plays an important role in the use of the material in the application. As stated above, a lower glass transition temperature and a lower thermoforming temperature generally facilitate an easier deformation of the sheet over dental mold material. The lower thermoforming temperature reduces fitting corrections due the difference in the coefficient of thermal expansion of the appliance material and the mold material. It is generally desired for the glass transition temperature of the material of the appliance to be less than that of polycarbonate. The glass transition temperature was measured in a Dynamic Mechanical Analyzer manufactured by TA Instruments. The rate of temperature change was 3° C./minute and the frequency rate was 1 Hz. The results are shown in Table 10.

TABLE 10

| PC/PCCD ratio | PC-type | PCCD-type | Tg (° C.)) |
|---|---|---|---|
| 50/50 | PC-1 | PCCD-2 | 109.8 |
| 50/50 | PC-1 | PCCD-3 | 109.8 |
| 50/50 | PC-2 | PCCD-2 | 111.7 |
| 50/50 | PC-2 | PCCD-3 | 111.7 |
| 60/40 | PC-1 | PCCD-2 | 118.1 |
| 60/40 | PC-1 | PCCD-3 | 118.1 |
| 60/40 | PC-2 | PCCD-2 | 119.9 |
| 60/40 | PC-2 | PCCD-3 | 119.9 |
| 70/30 | PC-1 | PCCD-2 | 126.2 |
| 70/30 | PC-1 | PCCD-3 | 126.2 |
| 70/30 | PC-2 | PCCD-2 | 128.0 |
| 70/30 | PC-2 | PCCD-3 | 128.0 |

From the Table 10 it may be seen that the glass transition temperature of the mixtures is at least about 25° C. less than the glass transition temperature of the polycarbonate and these lower glass transition temperatures can facilitate the thermoforming of the sheet over a mold of a dental image.

As noted above, it is desirable for the material of the appliance to display a percent stress retention effective to facilitate the repositioning of the teeth. Since each appliance is used to reposition the teeth over a period of time, it is desirable for the sheet to display a high percent stress retention (e.g., greater than of equal to about 60%) over the course of the utility of the appliance in the oral cavity. The samples shown in the Table 11 were subjected to stress retention tests for 12 hours in a manner similar to that detailed in Example 1. The results are shown in the Table 11.

TABLE 11

| PC/PCCD-ratio | PC-type | PCCD-type | Stress retention (%) |
|---|---|---|---|
| 100/0 | PC-2 | — | 87.2 |
| 0/100 | — | PCCD-2 | 25.5 |
| 0/100 | — | PCCD-3 | 36.0 |
| 60/40 | PC-2 | PCCD-3 | 78.4 |
| 50/50 | PC-2 | PCCD-2 | 73.22 |

From the table it may be seen that the mixtures have a higher percent stress retention than the samples containing only PCCD. Further it may be noted that the mixtures have a percent stress retention of greater than or equal to about 60%, which makes them useful in dental appliances for repositioning teeth.

The sheets were also subjected to studies to determine their optical clarity, yellowness index, and the like. The test methodology is detailed in Example 1. The results are shown in the Table 12.

TABLE 12

| PC/PCCD ratio | PC-type | PCCD-type | YI | Transmission | Haze |
|---|---|---|---|---|---|
| 50/50 | PC-1 | PCCD-2 | 2.65 | 89.2 | 1.89 |
| 50/50 | PC-1 | PCCD-3 | 2.65 | 89.2 | 2.1 |
| 50/50 | PC-2 | PCCD-2 | 2.65 | 89.2 | 1.89 |
| 50/50 | PC-2 | PCCD-3 | 2.65 | 89.2 | 2.1 |
| 60/40 | PC-1 | PCCD-2 | 2.65 | 89.2 | 1.63 |
| 60/40 | PC-1 | PCCD-3 | 2.65 | 89.2 | 1.72 |
| 60/40 | PC-2 | PCCD-2 | 2.65 | 89.2 | 1.63 |
| 60/40 | PC-2 | PCCD-3 | 2.65 | 89.2 | 1.72 |
| 70/30 | PC-1 | PCCD-2 | 2.65 | 89.2 | 1.34 |
| 70/30 | PC-1 | PCCD-3 | 2.65 | 89.2 | 1.37 |

TABLE 12-continued

| PC/PCCD ratio | PC-type | PCCD-type | YI | Transmission | Haze |
|---|---|---|---|---|---|
| 70/30 | PC-2 | PCCD-2 | 2.65 | 89.2 | 1.34 |
| 70/30 | PC-2 | PCCD-3 | 2.65 | 89.2 | 1.37 |

YI = yellowness index

From the Table 12, it may be seen that the yellowness index and the transmission of the sheet does not change with either molecular weight or the weight ratio of the polycarbonate of the PCCD in the mixture. A slight decrease in haze is observed with the increase in the molecular weight of the polycarbonate as well as with the increase in the weight fraction of polycarbonate.

The sheets were also subjected to lipid resistance tests. The lipid resistance test is conducted as per ISO 4599. Molded tensile bars were placed under fixed strains and contacted with a paper that was immersed in the lipids. The tensile properties are measured prior to and after contacting the paper and the results are compared. The paper was contacted with the neck of the molded tensile bar, wrapped in aluminum foil and sealed in a plastic bag. The contact period can vary from 3 to 7 days. The results shown in Table 13 were for samples tested for tensile properties after 3 days.

TABLE 13

| PC/PCCD ratio | PC-type | PCCD-type | Yield stress retention | Elongation @ break retention |
|---|---|---|---|---|
| 100/0 | PC-2 | — | 94.8 | 89.9 |
| 50/50 | PC-2 | PCCD-2 | 93.4 | 43.5 |
| 60/40 | PC-2 | PCCD-2 | 95.1 | 97.1 |

From the table it may be seen that ratio of the respective components in the mixture plays an important role in the retention of the elongation at break. From Examples 1 and 2, it may be seen that mixtures of polycarbonate and PCCD, in weight ratios of 50:50, 60:40, and 70:30, respectively display suitable properties for manufacturing a dental appliances for repositioning the teeth. As noted above, these mixtures permit the manufacturing of appliances that can facilitate the repositioning of the teeth, while presenting an aesthetically pleasing appearance. In addition, they can be thermoformed at temperatures of less than or equal to about 130° C., which permits the manufacturing of appliances that can be tailored to adequately fit a patients oral cavity.

The mixtures of polycarbonate and PCCD are also superior in their mechanical and optical properties to other commercially available dental products and appliances, which are primarily elastomeric in nature. In general the superior mechanical properties of the mixtures of polycarbonate and PCCD over other commercial appliances permits a smaller number of appliances to be utilized since each appliance can be used for longer periods of time. The transparency of the mixtures of polycarbonate and PCCD also make them more aesthetically pleasing than the commercially available appliances.

Example 3

In this example, a sheet made from a polycarbonate-PCCD mixture in a 60:40 weight ratio (Sample 5 from Example 1) was compared with a polyester urethane sheet. The polyester urethane sheet is commercially available as ISOPLAST 2530 from Dow Chemical at Midland, Mich. The sheets both had thicknesses of 30 mils (750 micrometers) and were made in the manner described in Example 1. The polycarbonate-PCCD had a matte/polish finish, while the polyester urethane sheet had a polish/polish finish. The sheets were subjected to stress retention and to stain resistance tests as detailed in Example 1. The results are shown in Table 14.

TABLE 14

| | Comparative Example | Sample 5 |
|---|---|---|
| Resin | PC/PCCD (60/40) | Polyester Urethane |
| Stress Relaxation (% Force Retention) after 3 hr | 89 | 78 |
| Stress Relaxation (% Force Retention) after 12 hr | 83 | 72 |
| Coffee Delta E | 0.21 | 0.57 |
| Ragu Delta E | 0.09 | 0.49 |

From the table it may be seen that both the stress retention and the stain resistance of the polycarbonate-PCCD mixture are superior to the polyester urethane mixture.

From the above experiments it may be seen that the sheets of the polycarbonate-PCCD mixture have a value of stress retention of greater than or equal to about 0.6, a stain resistance that is greater than a polyester urethane mixture, tensile properties that facilitate the repositioning of the teeth in less than or equal to about 40 steps. The polymeric mixtures may also be used in other dental applications such as dental retainer appliances, that may be used for retaining teeth in a desired position as well as other devices that can be used to prevent patients from grinding their teeth during their sleep.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An appliance for use in an oral cavity, wherein the appliance comprises a stain resistant polymeric shell that has cavities designed to receive teeth, and wherein the shell comprises a thermoplastic polymeric mixture that comprises a polycarbonate and a cycloaliphatic polyester, wherein the polycarbonate is present in an amount of about 50 wt % to about 90 wt % and wherein the weight percents are based on a total weight of a mixture that comprises polycarbonate and cycloaliphatic polyester.

2. The appliance of claim 1, wherein the polymeric mixture further comprises an additional thermoplastic polymer.

3. The appliance of claim 2, wherein the thermoplastic polymer is a polyolefin, polyamide, polyarylate, polyimide, polyacetal, polyacrylic, polystyrene, polyamideimide, polyacrylate, polymethacrylate, polyurethane, polyarylsulfone, polyethersulfone, polyarylene sulfide, polysulfone, polyetherimide, polytetrafluoroethylene, polyetherketone, polyether etherketone, polyarylene ether, polydimethylsiloxane, liquid crystalline polymer, polybenzoxazole, polyoxadiazole, polybenzothiazinophenothiazine, polybenzothiazole, polypyrazinoquinoxaline, polypyromellitimide, polyquinoxaline, polybenzimidazole, polyoxindole, polyoxoisoindoline, polydioxoisoindoline, polytriazine, polypyridazine, polypiperazine, polypyridine, polypiperidine, polytriazole, polypyrazole, polypyrrolidine, polycarborane, polyoxabicyclononane, polydibenzofuran, polyphthalide, polyacetal, polyanhydride, polyvinyl ether, polyvinyl thioether, polyvinyl alcohol, polyvinyl ketone, polyvinyl halide, polyvinyl nitrile, polyvinyl ester, polysulfonate, polythioester, polysulfonamide, polyurea, polyphosphazene, polysilazane, or a combination comprising at least one of the foregoing thermoplastic polymers.

4. The appliance of claim 1, wherein the cycloaliphatic polyester has recurring units of formula (VIII)

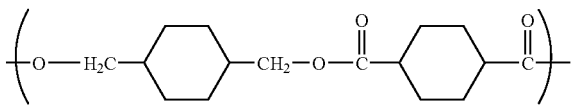

5. The appliance of claim 1, wherein the cycloaliphatic polyester is polyethelene terephthalate, polybutylene terephthalate, poly(1,4-cyclohexane-dimethanol-1,4-cyclohexanedicarboxylate), poly(trimethylene terephthalate), poly(cyclohexanedimethanol-co-ethylene terephthalate), poly(ethylene naphthalate), poly(butylene naphthalate), or a combination comprising at least one of the foregoing cycloaliphatic polyesters.

6. The appliance of claim 1, wherein the polycarbonate has a number average molecular weight of about 500 to about 1,000,000 grams/mole and the cycloaliphatic polyester has a molecular weight of about 500 to about 1,000,000 grams/mole.

7. The appliance of claim 6, wherein polycarbonate has a number average molecular weight of about 9,000 to about 38,000 grams/mole and the cycloaliphatic polyester has a molecular weight of about 40,000 g/mole to about 55,000 grams/mole.

8. The appliance of claim 1, wherein the polymeric mixture has an elastic modulus of greater than or equal to about 1,500 Newton/square millimeter when measured in tensile deformation at a rate of 2 millimeters/minute at room temperature, prior to use in an oral cavity.

9. The appliance of claim 1, wherein the polymeric mixture has a percent stress retention of greater than or equal to about 40%, prior to use in an oral cavity.

10. The appliance of claim 1, wherein the polymeric mixture has a stain resistance Delta F of less than or equal to about 2, prior to use in the oral cavity.

11. The appliance of claim 1, wherein the polymeric mixture has a yellowness index of less than or equal to about 1 and a percent haziness of less than or equal to about 0.5, prior to use in an oral cavity.

12. The appliance of claim 1, wherein the polymeric mixture has a percent stress retention of greater than or equal to about 40%, an elastic modulus of greater than or equal to about 1,500 Newton/square millimeter when measured in tensile deformation at a rate of 2 millimeters/minute at room temperature, a stain resistance Delta E of less than or equal to about 2, a yellowness index of less than or equal to about 1 and a percent haziness of less than or equal to about 0.5, prior to use in an oral cavity.

13. The appliance of claim 1, wherein the polymeric shell has a thickness of about 125 to about 1,250 micrometers.

14. The appliance of claim 1, wherein the polymeric shell comprises two or more layers.

15. The appliance of claim 14, wherein one layer comprises an elastomer.

16. The appliance of claim 1, wherein the appliance is part of a system of appliances designed to reposition teeth.

17. A method for maintaining or repositioning teeth in the oral cavity comprising:

placing an appliance in a patient's mouth, wherein the appliance comprises a stain resistant polymeric shell having cavities designed to receive teeth, and wherein the appliance comprises a polymeric mixture, that comprises a polycarbonate and a cycloaliphatic polyester; wherein the polycarbonte is present in an amount of about 50 wt % to about 90 wt %; and wherein the weight percents are based on a total weight of the polymeric mixture.

18. The method of claim 17, wherein additional appliances may be placed in a patient's mouth, and wherein a tooth position defined by a single cavity in each successive appliance differs from that defined in a prior appliance by an amount of no more than 2 millimeters.

* * * * *